United States Patent [19]

Lens et al.

[11] Patent Number: 5,482,832
[45] Date of Patent: Jan. 9, 1996

[54] HYBRIDIZATION ASSAYS USING ENZYME-LINKED PROBES

[75] Inventors: Peter F. Lens, Den Bosch; Tim Kievits, Vught, both of Netherlands

[73] Assignee: Akzo Nobel N.V., Arnhem, Netherlands

[21] Appl. No.: 320,203

[22] Filed: Oct. 7, 1994

Related U.S. Application Data

[63] Continuation of Ser. No. 910,860, Jul. 8, 1992, abandoned.

[51] Int. Cl.[6] .............................. C12Q 1/70; C12Q 1/68; C12P 19/34
[52] U.S. Cl. .................... 435/5; 435/6; 435/91.2
[58] Field of Search .................... 435/5, 6, 91.2; 935/78; 536/24.3, 25.32

[56] References Cited

U.S. PATENT DOCUMENTS

| | | | |
|---|---|---|---|
| 4,136,094 | 1/1979 | Condie | 260/122 |
| 4,521,511 | 6/1985 | Stout | 435/28 |
| 4,962,029 | 10/1990 | Levenson et al. | 435/192 |

FOREIGN PATENT DOCUMENTS

| | | |
|---|---|---|
| 0244207 | 7/1931 | European Pat. Off. . |
| 3917436 | 12/1989 | Germany . |

OTHER PUBLICATIONS

Lehninger, "*Principles of Biochemistry*", Worth Publishers, Inc., N.Y., 1982, pp. 128–129.

J. L. Guesdon et al., "Solid Phase Hybridization," Ann. Biol. Clin., vol. 48, pp. 479–488, 1990, France.

J. Flores et al., "Genetic Relatedness Among Animal Rotaviruses," Archives of Virology, vol. 87, pp. 273–285, 1986.

J. Flores et al., "Genetic Relatedness Among Human Rotaviruses," Journal of Medical Virology, vol. 17, pp. 135–143, 1985.

R. Kumar et al., "A Method for the Rapid Screening of Human Blood Samples for the Presence of HIV–1 Sequences: The Probe Shift Assay," AIDS Research and Human Retroviruses, vol. 5, No. 3, pp. 345–353, 1989, USA.

R. Kumar et al., "On–Line Fluorescent Detection of Assymetrically Amplified HIV–1 DNA Sequences," Technique, A Journal of Methods in Cell and Molecular Biology, vol. 2, No. 2, pp. 101–108, Apr. 1990.

J. L. McKimm–Breschkin, "The Use of Tetramethylbenzidine for Solid Phase Immunoassays," The Journal of Immunological Methods, vol. 135, pp. 277–280, 1990, The Netherlands.

*Primary Examiner*—W. Gary Jones
*Assistant Examiner*—Kenneth R. Horlick
*Attorney, Agent, or Firm*—Mary E. Gormley; William M. Blackstone

[57] ABSTRACT

The present invention is directed to hybridization assays using enzyme-linked oligonucleotide probes, whereby hybridization is detected by separating the hybridized labelled oligonucleotide from the unhybridized probe by gel electrophoresis

7 Claims, 1 Drawing Sheet

5,482,832

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:

(A) LENGTH: 55 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:1:

AATTCTAATA CGACTCACTA TAGGGGTGCT ATGTCACTTC CCCTTGGTTC TCTCA    55

(2) INFORMATION FOR SEQ ID NO:2:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:2:

AGTGGGGGA CATCAAGCAG CCATGCAAA    29

(2) INFORMATION FOR SEQ ID NO:3:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:3:

GAGACCATCA ATGAGGAAGC TGCAGAATGG GAT    33

(2) INFORMATION FOR SEQ ID NO:4:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:4:

AATTCTAATA CGACTCACTA TAGGGAGACT TGCTCACATC ATGCAGCT    48

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:5:

GACCCTTTCG AGGAGATGAA G    21

(2) INFORMATION FOR SEQ ID NO:6:

(i) SEQUENCE CHARACTERISTICS:
(A) LENGTH: 24 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:6:

GGATAAGCGG GAGATGTGGA TGGC    24

HYBRIDIZATION ASSAYS USING ENZYME-LINKED PROBES

This is a continuation of U.S. Ser. No. 07/910,860, filed Jul. 8, 1992, now abandoned.

BACKGROUND OF THE INVENTION

1. Field of the Invention

The present invention relates to a method for the detection and/or determination of nucleic acid in which the nucleic acid is hybridized to a labelled oligonucleotide, comprising a nucleic acid sequence complementary to at least part of the nucleic acid to be detected and/or determined, thereby forming a duplex nucleic acid which is separated from unhybridized labelled oligonucleotide by gel electrophoresis prior to detection of the labelled duplex nucleic acid in a gel.

2. Description of the Prior Art

Kumar et al. have described a method, the "probe shift assay" for the detection of PCR amplified DNA sequences In one of their publications, AidsResearchandHumanRetroviruses, Vol. 5, No. 3, 345–353, 1989, an assay is described in which HIV sequences were detected in PCR amplified DNA samples by adding a $^{32}$P-radioactive labelled oligonucleotide to a sample containing amplified DNA, and hybridizing the oligonucleotide to the amplified and denatured DNA. After the radioactive labelled oligonucleotide and amplified DNA were annealed, the heteroduplex formed was separated from the free radioactive labelled oiigonucleotide by gel electrophoresis on a non denaturing polyacrylamide gel. Following gel electrophoresis an X-ray film was exposed to the gel.

One disadvantage of such a system is that long exposure times -up to several hours- are required for detection of the radio labelled oligonucleotide in the gel. Another disadvantage of this system is that the use of radioactive material requires that these assays be performed by specially trained personnel in laboratories well adapted for the use of radioactive material.

In another article of Kumar et al., Technique, Vol. 2, No. 2, 101–108, 1990, an assay is described, based on the same principle, in which fluorescent labelled oligonucleotides were used instead of the previously described radioactive oligonucleotides. A 32-mer oligonucleotide was modified during synthesis by the attachment of fluorescein molecules to T residues. The label can now be detected in the gel by laser excitation. This method however requires the use of complicated laser instrumentation and is therefore not generally suitable for diagnostic purposes.

SUMMARY OF THE INVENTION

The present invention is characterized in that an enzyme labelled oligonucleotide is used.

An assay is provided for the detection of nucleic acid in a sample where the nucleic acid is amplified and an enzyme labelled oligonucleotide is added, the enzyme labelled oligonucleotide generally being an oligomer comprising a sequence complementary to at least part of the sequence of the nucleic acid optionally present in the sample. The enzyme labelled oligonucleotide is capable of forming a duplex nucleic acid with the complementary, amplified, nucleic acid by nucleic acid hybridization in the sample. Part of the amount of the oligonucleotides added will bind specifically to the amplified nucleic acid and the rest of the oligonucleotide added in excess will remain as free enzyme labelled olgonucleotide and will be separated from the labelled duplex nucleic acid by gel electrophoresis.

The nucleic acid, optionally present in a sample, is preferably amplified prior to reacting with the enzyme labelled oligonucleotide. For the amplification of the nucleic acid to be detected in the sample any suitable amplification technique can be used. A useful amplification technique is for example the NASBA technique described in EP 329.822, but also PCR (U.S. Pat. No. 4,683,202) and TAS (WO8810315) can be used. The advantage of the use of NASBA over the use of, for example PCR and TAS, is that no denaturation step is required to obtain single stranded nucleic acid after amplification is completed, since NASBA generates (large amounts of) single stranded RNA from the nucleic acid present, where the nucleic acid originally present can be RNA as well as DNA. The assay according to the invention can be used for the detection of RNA as well as DNA in a sample. For example, clinical (blood) samples can be tested on the presence of RNA from a virus like HIV, HCV or CMV. In fact any type of nucleic acid for which suitable amplification primers and a suitable enzyme labelled detection oligonucleotide can be constructed can be detected with an assay according to the invention.

The enzyme label retains its activity after it has been subjected to electrophoresis and locked in the gel system, and is still capable of reacting with an appropriate substrate to give a colour reaction by which the presence of the labelled nucleic acid (that is the enzyme labelled duplex nucleic acid and/or the free enzyme labelled oligonucleotide) in the gel is indicated.

The use of an enzyme labelled oligonucleotide has several advantages. The system is far less complicated compared to methods known in the art. No special instrumentation is required for the detection of the enzyme label in the gel and therefore the assay according to the invention is very useful for diagnostic purposes, e.g. the testing of clinical samples on the presence of a certain nucleic acid originating from, for example, a certain virus.

Since, with a method according to the invention, nucleic acid amplification may be coupled to an enzymatic signal amplification (each enzyme molecule will be able to convert many substrate molecules that will stay in/on the gel) a high sensitivity is obtained.

DESCRIPTION OF THE PREFERRED EMBODIMENTS

Figure 1:
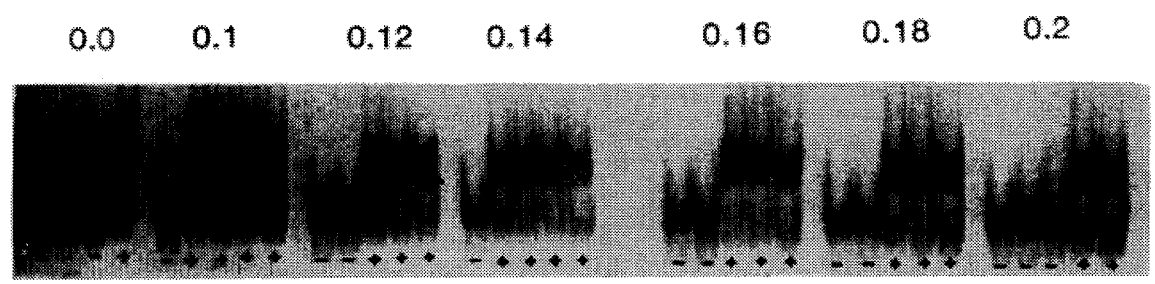
FIG. 1 is a picture of he gels representing the results of the gel assays of Example 1.

Separation of nucleic acid strands that differ in size by gel electrophoresis is a well-known technique. The gel is a complex network of polymeric molecules like polyacrylamide or agarose. Under an electric field nucleic acid molecules migrate through the gel because of their negative charge. Different molecules have different mobilities in the gel depending on the mass, charge and shape of each molecule; a small nucleic acid molecule can easily thread its way through the gel and hence migrates faster than a larger molecule.

With a method according to the invention two complexes, both comprising the same enzyme label, are separated on a gel by electrophoresis.

Enzymes, like for example horse radish peroxidase, usually do not migrate through gels used for the separation of nucleic acid strands. Surprisingly, with a method according to the invention where the enzyme is coupled to a oligonucleotide, the enzyme does enter the gel and traverses it with a speed that depends on the length and charge of the nucleic acid to which it is attached. An excellent separation of the free enzyme labelled oligonucleotide from the enzyme labelled duplex is obtained.

After separation of the remaining free enzyme labelled oligonucleotide from the enzyme labelled duplex nucleic acid by gel electrophoresis is completed, detection and/or determination of the labelled duplex in the gel is carried out by staining with an appropriate enzyme substrate.

The staining procedure is simple and fast. The gel is simply soaked in a solution comprising an appropriate enzyme substrate and a colour reaction takes place between the enzyme label present in the gel and the substrate solution. The substrate used will react with bands, containing enzyme-labelled nucleic acid, present in the gel.

The colour reaction between the enzyme label and the substrate will take place on or in the gel and the presence of the colour on or in the gel, indicating the presence of enzyme activity, can be detected visually.

The substrate used for the coloration of the enzyme label containing bands in the gel can be a precipitating substrate like for example 4-chloro-1 naphtol. The soluble form of a precipitating substrate is converted into a coloured insoluble form by the enzyme present in the gel and the insoluble form precipitates on the gel. The precipitation of the substrate on the gel specifically indicates the position of the enzyme containing bands.

Preferably, however, a substrate is used that is converted into a non-precipitating product by the enzyme label present in the gel. The soluble form of a non-precipitating substrate is converted into a non-precipitating product by the enzyme present in the gel and the converted non-precipitating substrate is immobilized on the gel. By using a non-precipitating substrate the sensitivity of the method is markedly improved.

To improve the attachment of a non-precipitating substrate to a gel it is preferred to use a gel composed of a mixture of gel materials to which dextran sulphate has been added. By adding dextran sulphate to the gel material a gel is obtained in which a substrate will be immobilized more effectively.

It is also possible to contact the gel with a dextran sulphate solution prior to reacting the gel with a substrate solution.

Good results are obtained with an assay according to the invention in which the oligonucleotide is labelled with horseradish peroxidase or a derivative thereof, and detection takes place by staining labelled nucleic acid in the gel with 3,3',5,5'-tetramethylbenzidine/$H_2O_2$. Horseradish peroxidase (HRP) catalyses the conversion of hydrogenperoxide into water. Tetramethylbenzidine (TMB), a non-precipitating substrate for HRP, is a chromogenic substance that acts as electron donor for the conversion of hydrogen peroxide into water and is converted by the HRP into a coloured complex thereby indicating the presence of enzyme activity. The colour formed can be detected visually.

The use of a HRP-TMB detection system has been described by Jennifer L. McKimm-Bresschkin in the JournalofImmunologicalMethods, vol. 135, 277–280, 1990 for the development of nitrocellulose membranes used in slot blots and Western blots. The membranes were treated with dextran sulphate prior to reaction with TMB. The system as described for nitrocellulose sheets, however, has not been applied for the coloration of nucleic acid bands directly in a gel as with the method according to the invention.

Of course the staining procedure must be carried out under conditions where the enzyme is still active. The staining solution should have a pH value that is appropriate for the enzyme label used.

Electrophoretic buffers usually have a pH value that differs from the activity optimum of the enzyme. Therefore the gel has to be brought to the proper pH value for the enzyme reaction to take place by washing the gel with a buffer solution after it has been subjected to electrophoresis.

When HRP is used as enzyme label the gel can be directly stained after it has been subjected to electrophoresis in a buffer comprising the enzyme substrate (e.g. TMB/$H_2O_2$) and imidazol. Imidazol shifts the activity optimum for HRP to a higher pH value. Therefore, with the use of imidazol, the gel can be directly stained in the electrophoretic buffer and the time consuming washing procedure can be eliminated.

The invention is further exemplified with the following examples:

EXAMPLE 1

Detection of in vitro generated wild type HIV-RNA.

In vitro generated wild type HIV-RNA was used as input material for amplification by NASBA as described in EP 329822, starting with different amounts of nucleic acid ($10^1$, $10^2$, $10^3$, $10^4$ molecules). As negative control for the amplification procedure a mixture without a template (NT) was used. A primer pair for the HIV-gene gag was used for amplification (Primer 1 (OT270): AATTCTAATACGACTCACTATAGGGGTGCTATGTCA CTTCCCCCTTGGTTCTCTCA; Primer 2: (OT271) AGTGGGGGGACATCAAGCAGCCATGCAAA). Amplification products were hybridized to a complementary HRP labelled oligonucleotide (OT399: GAGACCATCAATGAGGAAGCTGCAGAATGGGAT) in a reaction mixture which included buffer components (sodium citrate, sodium chloride, glycerol, EDTA) and bromophenol blue and xylene cyanol as electrophoretic markers. Hybridization was performed for 10 minutes at 45° C. in a water bath. A 7% native acrylamide gel in a Biometra Multigel G44 configuration was used for separation of the hybridized and the non-hybridized HRP labelled oligonucleotide. 1*TBE (50 mM Tris, 50 mM Borate, 1 mM EDTA, pH 8,5) was used as running and gel buffer. 2,5 µl of the hybridized samples were put on the gel. The electrophoresis was stopped when xylene cyanol reached 70% of the gel length. After gel electrophoresis was completed the gel was washed and rocked in citrate buffer pH 5,0 for 5 minutes. Subsequently the gel was washed and rocked in citrate buffer pH 5,0 containing 1% dextran sulphate for 15 minutes prior to being rocked and washed for two minutes in citrate buffer pH 5,0 again. HRP containing bands were visualised by staining with TMB (0.1 mg/ml) and $H_2O_2$ (1µl 30% $H_2O_2$ per 10 ml) for 10 minutes. The gel was rinsed with water and incubated (dehydrated) for at least two hours in 50% methanol. Afterwards the gel was dried for two hours at 50° C. under vacuum in a geldryer (Bio-rad model 583). Banding patterns were scored visually. In all lanes a band of free HRP labelled oligonucleotide was visible. In the lane with a positive signal a more retarded band for the duplex is present.

Table 1 gives the results of the gel assays for the different amounts of wildtype HIV-1 RNA ($10^1$, $10^2$, $10^3$, $10^4$ molecules) where different amounts of RNase H were used during the NASBA amplification procedure.

TABLE 1

ELGA DETECTION WITH DIFFERENT RNASE H CONCENTRATIONS.

| | RNase H (U/25 μl) | | | | | | |
|---|---|---|---|---|---|---|---|
| | 0.00 | 0.10 | 0.12 | 0.14 | 0.16 | 0.18 | 0.20 |
| NT | − | − | − | − | − | − | − |
| $10^1$ | − | + | − | + | − | − | − |
| $10^2$ | − | + | + | + | + | + | − |
| $10^3$ | − | + | + | + | + | + | + |
| $10^4$ | + | + | + | + | + | + | + |

FIG. 1 is a picture of the gels representing the data as given in Table 1. Positive samples give two bands in the gel (one for the free enzyme labelled oligonucleotide at the bottom of the gel and one band representing the formed duplex).

EXAMPLE 2

Detection of HIV nucleic acid isolated from whole blood samples.

Nucleic acid was extracted from whole blood samples of SCID-hu mice infected with HIV-1. The samples were processed according to the sample processing method as described by Boom et al. (J.Clin.Microbiol.28:495–503,1990). RNA was preferentially amplified by using the isolated nucleic acid as input for NASBA. Every four to five samples a $H_2O$ aliquot was included (no template, NT) to check contamination. As positive control a series containing different amounts of invitro generated wildtype HIV-1 RNA ($10^1$, $10^2$, $10^3$, $10^4$ molecules) was used. The amplification primer pair and the HRP labelled detection oligonucleotide as described in example 1 were used. $H_2O$ aliquots were used as negative control for hybridization. The electrophoresis and staining procedures were performed in the same way as already described in example 1. Results are given in Table 2.

TABLE 2

ELGA SCORES OF HIV-1 INFECTED HU-SCID MICE.

| sample | 1st | 2nd | comment |
|---|---|---|---|
| 1 | − | − | negative |
| 2 | − | − | negative |
| 3 | − | − | negative |
| 4 | − | − | negative |
| 5 | + | + | positive |
| 6 | − | − | negative |
| 7 | − | − | negative |
| 8 | + | − | indeterminate |
| 9 | − | − | negative |
| 10 | − | − | negative |
| NT1 | − | − | negative |
| NT2 | − | − | negative |
| NT3 | − | − | negative |
| NT4 | − | − | negative |
| NT5 | − | − | negative |
| $10^1$ | − | − | negative |
| $10^2$ | − | + | indeterminate |
| $10^3$ | + | + | positive |
| $10^4$ | + | + | positive |
| $10^5$ | + | + | positive |
| $H_2O$ 1 | − | − | negative |
| $H_2O$ 2 | − | − | negative |
| $H_2O$ 3 | − | − | negative |
| $H_2O$ 4 | − | − | negative |

EXAMPLE 3

Detection of cytomegalovirus (CMV)-PCR products of the Immediate Early (IE) Exon 5 region.

Nucleic acid is isolated from 1 ml. of ten full blood samples according to the method described by Boom et al. (J.Clin.Microbiol. 28: 495–503, 1990). A twentieth part of the isolated nucleic acid was used for first strand cDNA syntheses in a standardly performed reaction (PCR protocol, Ed. Innis et al., page 51, Academic Press, 1990) using primer OT578 (AATTCTAATACGACTCACTATAGG-GAGACTTGCT CACATCATGCAGCT) for 1 hr at 37° C. The cDNA was then used as template for PCR cycling 1 min. 95° C., 1.5 min. 52° C. and two min. 72° C. The primers used were OT578 and ORG567 (GACCCTTTCGAGGAGATGAAG). In this experiment positive and negative controls were added to monitor contamination events and sensitivity of the PCR. After forty cycles the samples were heated for 5 min. to 95° C. and cooled on ice. Two μl of these samples were hybridized with an oligonucleotide-HRP specific for an internal sequence of the amplificate (GGATAAGCGG-GAGATGTGGATGGC) and processed for Enzyme linked Gel Assay according to example 1. After staining the following results were obtained: Patients 1, 2, 3, 5, 6, 8 and 9 were positive and patients 4, 7 and 10 were negative. The positive controls showed the experiment to be very sensitive (10 in vitro generated RNA molecules containing the IE region could be detected) and all negative controls showed no signal on the gel.

We claim:

1. A method for detecting nucleic acid in a sample, in which the nucleic acid is hybridized to a labelled oligonucleotide, comprising: adding an enzyme labelled nucleic acid complementary to at least part of the nucleic acid to be detected to the sample, hybridizing the labelled nucleic acid with the nucleic acid to be detected to form a duplex nucleic acid, separating the duplex nucleic acid from the unhybridized labelled nucleic acid by gel electrophoresis and detecting the hybridized labelled nucleic acid on the electrophoresis gel, wherein enzyme label is horseradish peroxidase and wherein detection takes place by staining enzyme labelled nucleic acid in the gel with an appropriate enzyme substrate.

2. The method according to claim 1, wherein the nucleic acid being detected is amplified prior to hybridizing with the enzyme labelled nucleic acid.

3. The method according to claim 1, wherein the enzyme substrate is converted into a non-precipitating product by the enzyme in the enzyme labelled nucleic acid in the duplex nucleic acid present in the gel.

4. The method according to claim 3, wherein the labelled nucleic acid in the gel is detected by staining with 3,3',5,5'-tetramethylbenzidine.

5. The method according to claim 1, wherein the gel comprises a mixture of gel materials to which dextran sulphate has been added.

6. The method according to claim 4, wherein the gel is stained in the presence of imidazol.

7. The method according to claim 1, wherein the nucleic acid is viral RNA.

* * * * *